US010216940B2

(12) United States Patent
Zwinger (10) Patent No.: US 10,216,940 B2
(45) Date of Patent: Feb. 26, 2019

(54) SYSTEMS, METHODS, APPARATUSES, AND COMPUTER PROGRAM PRODUCTS FOR TRUNCATED, ENCRYPTED SEARCHING OF ENCRYPTED IDENTIFIERS

(71) Applicant: Change Healthcare Holdings, LLC, Nashville, TN (US)

(72) Inventor: Mike Zwinger, Savage, MN (US)

(73) Assignee: CHANGE HEALTHCARE HOLDINGS, LLC, Nashville, TN (US)

( * ) Notice: Subject to any disclaimer, the term of this patent is extended or adjusted under 35 U.S.C. 154(b) by 875 days.

(21) Appl. No.: 14/671,031

(22) Filed: Mar. 27, 2015

(65) Prior Publication Data

US 2016/0283661 A1  Sep. 29, 2016

(51) Int. Cl.
*G06F 21/60* (2013.01)
*G06F 21/62* (2013.01)
*G16H 10/60* (2018.01)
*G06F 19/00* (2018.01)

(52) U.S. Cl.
CPC ............ *G06F 21/602* (2013.01); *G06F 19/00* (2013.01); *G06F 21/6254* (2013.01); *G16H 10/60* (2018.01); *G06Q 2220/00* (2013.01)

(58) Field of Classification Search
CPC ..................... G06F 17/30985; G06F 17/30321
USPC ........................................................ 705/2–4
See application file for complete search history.

(56) References Cited

U.S. PATENT DOCUMENTS

| | | | |
|---|---|---|---|
| 2004/0122656 A1* | 6/2004 | Abir | G06F 17/2872 704/4 |
| 2005/0165623 A1* | 7/2005 | Landi | G06F 21/6254 705/2 |
| 2011/0246470 A1* | 10/2011 | Negrassus | G06F 17/30312 707/741 |
| 2013/0238646 A1* | 9/2013 | Maro | G06F 21/6227 707/758 |

FOREIGN PATENT DOCUMENTS

WO    WO-2008065351 A1 *  6/2008  ......... G06F 21/6272

OTHER PUBLICATIONS

Goh, Eu-Jin, "Secure Indexes," May 5, 2004 (Year: 2004).*

* cited by examiner

*Primary Examiner* — Elaine Gort
*Assistant Examiner* — John P Go
(74) *Attorney, Agent, or Firm* — Alston & Bird LLP (57) ABSTRACT

Methods, apparatuses, and computer program products are provided for truncated, encrypted searching of encrypted identifiers. A method may include receiving patient information associated with a plurality of patients and including a patient identifier of a sequence of characters for each of the plurality of patients. Methods may further include: extracting a first subset of the sequence of characters from each of the patient identifiers; encrypting the first subset of the sequence of characters from each of the patient identifiers to form a first truncated encrypted identifier for each of the plurality of patients; encrypting each of the patient identifiers to create an encrypted patient identifier for each of the plurality of patients; and storing the first truncated encrypted identifiers and the encrypted patient identifiers for each of the plurality of patients.

17 Claims, 4 Drawing Sheets

SYSTEMS, METHODS, APPARATUSES, AND COMPUTER PROGRAM PRODUCTS FOR TRUNCATED, ENCRYPTED SEARCHING OF ENCRYPTED IDENTIFIERS

TECHNOLOGICAL FIELD

Embodiments of the present invention relate generally to the searching of encrypted information and, more particularly, to methods, apparatuses, and computer program products for truncated, encrypted searching of encrypted identifiers.

BACKGROUND

In a variety of industries and settings it is imperative to maintain data security in order to ensure the privacy of customers, clients, employees, etc. A preferred way of maintaining data security is through the use of encryption. Various forms of encryption may be used to encrypt information and multiple layers of encryption or protection may be used to protect sensitive data.

One industry, for which data protection is not only desirable but mandated, is the healthcare industry. The healthcare industry is moving toward maintaining healthcare records electronically. In this regard, the evolution of modern computing and networking technology has lead to a widespread adoption and increasing reliance on computers and associated software for facilitating patient treatment, maintaining patient treatment records, and for tracking and payment of charges attendant to patient treatment. For example, use of computing technology by health service providers has allowed for the creation and maintenance of electronic health record documents for patients, including medical treatment and diagnosis records, billing records, insurer explanation of benefits records, and payment records. Electronic maintenance of such records has offered several advantages to health service providers, including more ready access to patient health information and a reduction in reliance on cumbersome paper files, which may be burdensome to maintain and may be more susceptible to data loss than electronic systems.

The reliance on electronic health records introduces challenges for securely maintaining patient information and maintaining compliance with the Health Insurance Portability and Accountability Act (HIPAA). HIPAA was developed, in part, to define rules required to protect the confidentiality and security of healthcare information. Compliance with HIPAA has added complexities to the handling of patient data, particularly while balancing ease-of-use for healthcare providers with the necessary security to maintain patient privacy. One added complexity for compliance with HIPAA includes a requirement to log access to protected healthcare data. When protected healthcare data, such as an electronic health record, is accessed, the access event must be logged to at least identify who accessed the information, what information was accessed, and the date and time of the access event. When a healthcare provider searches for patient information, they may access a plurality of patients in an effort to locate the specific patient they are looking for. A log of each record that is accessed must be created such that a search for a single patient may result in dozens or hundreds of access events that must be logged. This requirement creates a substantial burden for the storage and maintenance of log files that can consume large amounts of data storage space.

BRIEF SUMMARY OF SOME EXAMPLES OF THE INVENTION

Systems, methods, apparatuses, and computer program products are herein provided for providing truncated, encrypted searching of encrypted identifiers. These systems, methods, apparatuses, and computer program products may provide several advantages to patients, health service providers, computers, and computing systems. In this regard, some example embodiments provide a secure patient information database system including at least one processor. The processor may be configured to cause the system to receive patient information associated with a plurality of patients and including a patient identifier for each of the plurality of patients, the patient identifier including a sequence of characters. The system may be caused to extract a first subset of the sequence of characters from each of the patient identifiers and encrypt the first subset of the sequence of characters from each of the patient identifiers to form a first truncated encrypted identifier for each of the plurality of patients. The system may be caused to encrypt each of the patient identifiers to create an encrypted patient identifier for each of the plurality of patients and store, for each of the plurality of patients, the first truncated encrypted identifiers and the encrypted patient identifiers. The first subset of the sequence of characters may include at least one, but less than all of the characters of the respective patient identifier.

According to some embodiments, the system may be caused to extract a second subset of the sequence of characters from each of the patient identifiers, encrypt the second subset of the sequence of characters from each of the patient identifiers to form a second truncated encrypted identifier for each of the plurality of patients, and store, for each of the plurality of patients, the second truncated encrypted identifier. The system may be caused to receive a search request including at least one search character, extract a first number of characters equivalent to the number of characters in the first subset of the sequence of characters from each of the patient identifiers in response to the search request including no more characters than in the first number of characters, and extract a second number of characters equivalent to the number of characters in the second subset of the sequence of characters from each of the patient identifiers in response to the search request including more characters than in the first subset of the sequence of characters. The system may be caused to encrypt the extracted first number of characters or the second number of characters to obtain an encrypted search string, compare the encrypted search string against the first truncated encrypted identifiers in response to the encrypted search string being encrypted from the first number of characters, and compare the encrypted search string against the second truncated encrypted identifiers in response to the encrypted search string being encrypted from the second number of characters.

Optionally, embodiments may cause the system to receive a search request including at least one search character, extract a number of characters equal to the number of characters in the first subset of the sequence of characters to form a first search string, encrypt the first truncated search string to obtain a first encrypted search string, and conduct a search of the first truncated encrypted identifiers to identify one or more first truncated encrypted identifiers that match the first encrypted search string. The system may be caused to decrypt the encrypted patient identifiers for each of the plurality of patients for which the first truncated encrypted identifier matches the first encrypted search string. The system may optionally be caused to provide for presentation of the patient identifiers for each of the plurality of patients for which the first truncated encrypted identifier matches the first encrypted search string.

Embodiments may provide a method for providing network-accessible patient health records. The method may include receiving patient information associated with a plurality of patients and including a patient identifier of a sequence of characters for each of the plurality of patients. Methods may include: extracting a first subset of the sequence of characters from each of the patient identifiers; encrypting the first subset of the sequence of characters from each of the patient identifiers to form a first truncated encrypted identifier for each of the plurality of patients; encrypting each of the patient identifiers to create an encrypted patient identifier for each of the plurality of patients; and storing the first truncated encrypted identifiers and the encrypted patient identifiers for each of the plurality of patients. The first subset of the sequence of characters may include at least one, but less than all of the characters of the respective patient identifier.

According to some embodiments, the method may include extracting a second subset of the sequence of characters from each of the patient identifiers, where the second subset is different from the first subset, encrypting the second subset of the sequence of characters from each of the patient identifiers to form a second truncated encrypted identifier for each of the plurality of patients, and storing the second truncated encrypted identifier for each of the plurality of patients. Methods may optionally include: receiving a search request including at least one search character; extracting a first number of characters equivalent to the number of characters in the first subset of the sequence of characters from each of the patient identifiers in response to the search request including no more characters than in the first number of characters; and extracting a second number of characters equivalent to the number of characters in the second subset of the sequence of characters from each of the patient identifiers in response to the search request including more characters than in the first subset of the sequence of characters. Methods may include: encrypting the extracted first number of characters or the second number of characters to obtain an encrypted search string; comparing the encrypted search string against the first truncated encrypted identifiers in response to the search string being encrypted from the first number of characters; and comparing the encrypted search string against the second truncated encrypted identifiers in response to the encrypted search string being encrypted from the second number of characters.

Optionally, embodiments of the method may include receiving a search request including at least one search character; extracting a number of characters equal to the number of characters in the first subset of the sequence of characters to form a first search string; encrypting the first truncated search string to obtain a first encrypted search string; and conducting a search of the first truncated encrypted identifiers to identify one or more first truncated encrypted identifiers that match the first encrypted search string. Methods may include decrypting the encrypted patient identifiers for each of the plurality of patients for which the first truncated encrypted identifier matches the first encrypted search string. Methods may optionally include providing for presentation of the patient identifiers for each of the plurality of patients for which the first truncated encrypted identifier matches the first encrypted search string.

Embodiments may provide a computer program product for providing network-accessible patient health records, the computer program product including at least one non-transitory computer-readable storage medium having program instructions stored therein. The computer-readable program instructions including program code instructions for receiving information associated with a plurality of patients and including a patient identifier of a sequence of characters for each of the plurality of patients. The computer program product may include: program code instructions for extracting a first subset of the sequence of characters for each of the patient identifiers; program code instructions for encrypting the first subset of the sequence of characters from each of the patient identifiers to form a first truncated encrypted identifier for each of the plurality of patients; program code instructions for encrypting each of the patient identifiers to create an encrypted patient identifier for each of the plurality of patients; and program code instructions for storing, for each of the plurality of patients, the first truncated encrypted identifiers and the encrypted patient identifiers. The first subset of the sequence of characters may include at least one, but less than all of the characters of the respective patient identifier.

According to some embodiments, the computer program product may include program code instructions for extracting a second subset of the sequence of characters from each of the patient identifiers; program code instructions for encrypting the second subset of the sequence of characters from each of the patient identifiers to form a second truncated encrypted identifier for each of the plurality of patients; and program code instructions for storing, for each of the plurality of patients, the second truncated encrypted identifiers. The computer program product of some embodiments may optionally include: program code instructions for receiving a search request including at least one search character; program code instructions for extracting a first number of characters equivalent to the number of characters in the first subset of the sequence of characters from each of the patient identifiers in response to the search request including no more characters than in the first number of characters; and program code instructions for extracting a second number of characters equivalent to the number of characters in the second subset of the sequence of characters from each of the patient identifiers in response to the search request including more characters than in the first subset of the sequence of characters. Computer program products may optionally include: program code instructions for encrypting the extracted first number of characters or the second number of characters to obtain an encrypted search string; program code instructions for comparing the encrypted search string against the first truncated encrypted identifiers in response to the encrypted search string being encrypted from the first number of characters; and program code instructions for comparing the encrypted search string against the second truncated encrypted identifiers in response to the encrypted search string being encrypted from the second number of characters.

Some embodiments of a computer program product may include: program code instructions for receiving a search request including at least one search character; program code instructions for extracting a number of characters equal to the number of characters in the first subset of the sequence of characters to form a first search string; program code instructions for encrypting the first truncated search string to obtain a first encrypted search string; and program code instructions for conducting a search of the first truncated encrypted identifiers to identify one or more first truncated encrypted identifiers that match the first encrypted search string. Embodiments may also include program code instructions for decrypting the encrypted patient identifiers for each of the plurality of patients for which the first truncated encrypted identifier matches the first encrypted search string.

The above summary is provided merely for purposes of summarizing some example embodiments of the invention so as to provide a basic understanding of some aspects of the invention. Accordingly, it will be appreciated that the above described example embodiments are merely examples and should not be construed to narrow the scope or spirit of the invention in any way. It will be appreciated that the scope of the invention encompasses many potential embodiments, some of which will be further described below, in addition to those here summarized.

BRIEF DESCRIPTION OF THE DRAWINGS

Having thus described embodiments of the invention in general terms, reference will now be made to the accompanying drawings, which are not necessarily drawn to scale, and wherein:

DETAILED DESCRIPTION

Some embodiments of the present invention will now be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like reference numerals refer to like elements throughout.

As used herein, the terms "data," "content," "information" and similar terms may be used interchangeably to refer to data capable of being transmitted, received, displayed and/or stored in accordance with various example embodiments. Thus, use of any such terms should not be taken to limit the spirit and scope of the disclosure. Further, where a computing device is described herein to receive data from another computing device, it will be appreciated that the data may be received directly from the another computing device or may be received indirectly via one or more intermediary computing devices, such as, for example, one or more servers, relays, routers, network access points, and/or the like.

Electronic health records (EHR), also known as electronic patient health records, patient health records (PHR), or clinical health records, are becoming increasingly popular with the ubiquity of personal computers, tablet computers, and other digital devices used in the patient care environment. These electronic health records are useful tools for both physicians and patients, and can increase the portability of a patient's personal health record information while helping providers better understand a patient under their care due to the longitudinal health record information available in an electronic health record. The availability of this information also brings opportunity to streamline access to the electronic health record while maintaining patient privacy.

The availability of patient information electronically has enhanced the patient experience by enabling providers in different locations to access a patient's medical records without having to transport physical files between the providers' locations. However, this availability can compromise the security of patients' information by potentially exposing healthcare data to unauthorized users. In order to mitigate this risk, encryption of healthcare data may be used such that any data that may be intercepted or stolen by an unauthorized user is useless without the proper decrypting means, generally maintained by authorized healthcare providers or by third party data security providers.

Figure 1:
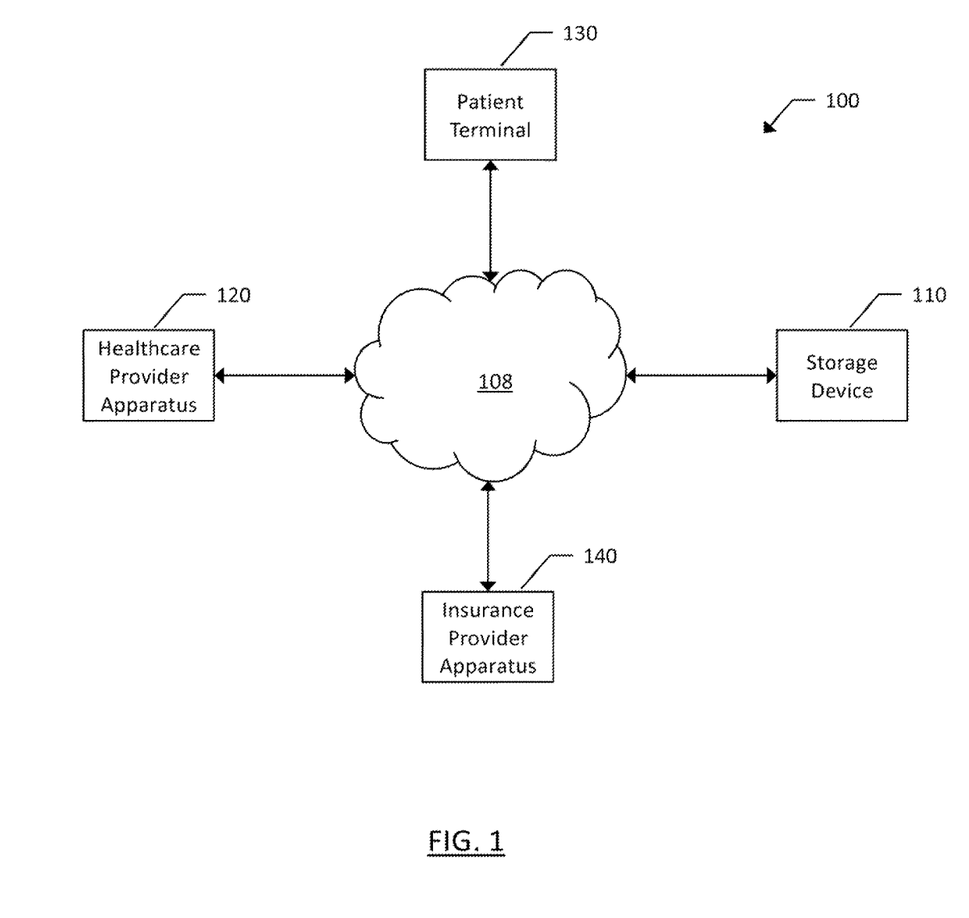
FIG. 1 illustrates a system for truncated, encrypted searching of encrypted identifiers according to some example embodiments.

FIG. 1 illustrates a simplified example embodiment of a healthcare network system 100. It will be appreciated that the system 100 as well as the illustrations in other figures are each provided as an example of some embodiments and should not be construed to narrow the scope or spirit of the disclosure in any way. In this regard, the scope of the disclosure encompasses many potential embodiments in addition to those illustrated and described herein. As such, while FIG. 1 illustrates one example of a configuration of a system for providing network-accessible electronic health records, numerous other configurations may also be used to implement embodiments of the present invention.

In the system of FIG. 1, electronic health records may be semantically networked and accessible from a plurality of access points. In this regard, in the system 100, a patient's electronic health records may exist in a secure database, accessible on a network, such as the internet. More particularly, patient electronic health record documents may be stored within a storage device 110 that may reside within a network 108. The network 108 may comprise one or more wireless networks (e.g., a cellular network, wireless local area network, wireless metropolitan area network, and/or the like), one or more wireline networks (e.g., a wired local area network), or some combination thereof, and in some embodiments comprises at least a portion of the internet. It will be appreciated that the storage device 110 may comprise any location or plurality of locations on the network 108 on which patient electronic health record documents may be stored and accessed via a secure user interface. In this regard, the storage device 110 may be supported by a "cloud" computing model supporting dynamically scalable and highly virtualized storage resources. The system may include a healthcare provider accessing the network 108 through healthcare provider apparatus 120, an insurance provider accessing the network 108 through insurance provider apparatus 140, and/or a patient accessing the network 108 via patient terminal 130, as will be described further below.

Security of electronic health record documents stored within the storage device 110 may be maintained through a variety of available means. For example, a layered security approach may be employed with encryption keys, public key infrastructure (PKI), extensible markup language (XML) encryption, etc. The electronic medical record of a patient stored on storage device 110 may be accessible to authorized users, such as a patient's physician, a nurse of a practice associated with the patient, a specialist conducting a reading (e.g., a radiologist conducting a radiology read order) on the patient, an in-home care-giver for a patient, a parent or guardian of the patient, a physician's office staff member, or the patient him/herself. The physicians, nurses, specialists, or other healthcare providers that may be authorized to access the electronic health record of a patient may collectively be referred to herein as authorized healthcare providers. Authorized healthcare providers may access a patient's electronic health record stored on storage device 110 through, for example, healthcare provider apparatus 120.

The healthcare provider apparatus 120 may be embodied as any computing device or plurality of computing devices configured to perform at least some functions of interfacing with an electronic health record as described herein. In this regard, the healthcare provider apparatus 120 may comprise an apparatus or plurality of apparatuses operated by an agency or entity interfacing with an electronic health record of a patient in accordance with one or more example embodiments. By way of non-limiting example, the healthcare provider apparatus 120 may be embodied as one or more servers, a server cluster, a cloud computing infrastructure, one or more network nodes, multiple computing devices in communication with each other, or any combination thereof, and/or the like. A healthcare provider apparatus 120 may be embodied as a computing apparatus at a physician's office, hospital, lab, therapist, pharmacy, insurance provider, patient guarantor, and/or other healthcare service provider. According to some embodiments, a healthcare provider apparatus 120 may include a personal computing device comprising sufficient security features to enable a healthcare provider access to a patient's electronic health record regardless of location, such as a remotely located radiologist performing a teleradiology study.

Figure 2:
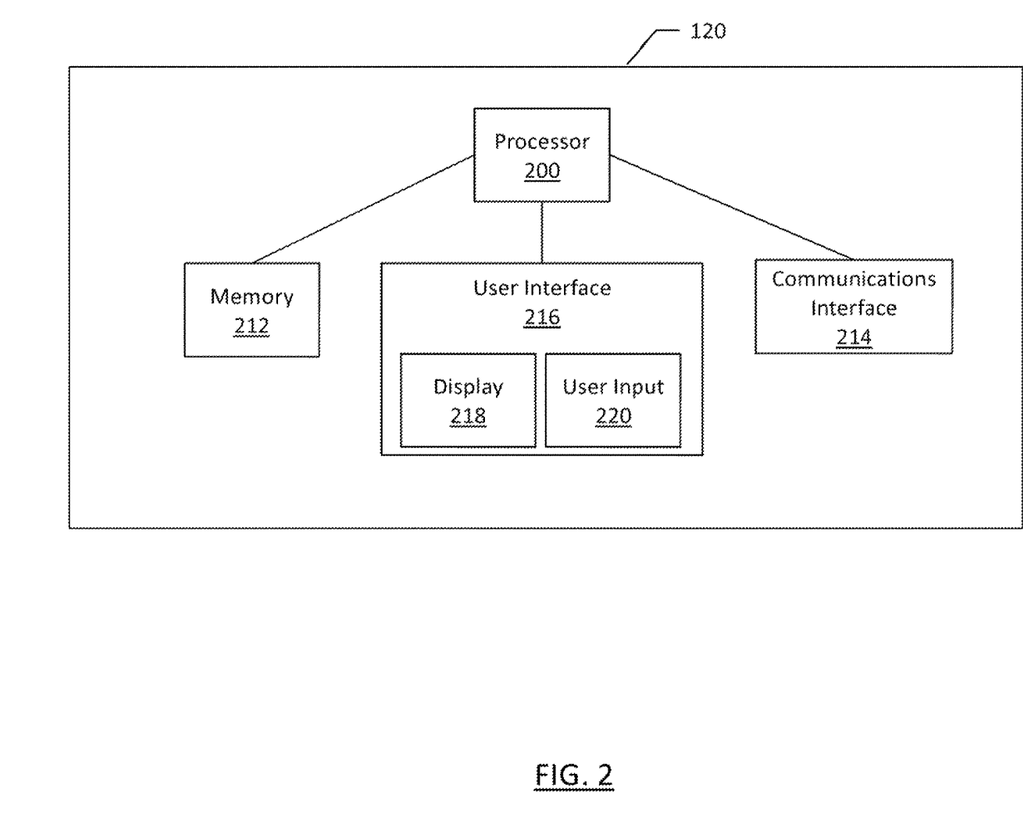
FIG. 2 illustrates a block diagram of an apparatus for conducting truncated, encrypted searching of encrypted identifiers according to some example embodiments.

FIG. 2 illustrates a block diagram of a healthcare provider apparatus 120 configured to interface with an electronic health record according to an example embodiment. In some example embodiments, the healthcare provider apparatus 120 includes various means for performing the various functions described herein. These means may include, for example, one or more of a processor 200, memory 212, communications interface 214, and a user interface 216. The means of the healthcare provider apparatus 120 as described herein may be embodied as, for example, circuitry, hardware elements (e.g., a suitably programmed processor, combinational logic circuit, and/or the like), a computer program product comprising computer-readable program instructions (e.g., software or firmware) stored on a computer-readable medium (e.g. memory 212) that is executable by a suitably configured processing device (e.g., the processor 200), or some combination thereof.

The processor 200 may, for example, be embodied as various means including one or more microprocessors, one or more coprocessors, one or more multi-core processors, one or more controllers, processing circuitry, one or more computers, various other processing elements including integrated circuits such as, for example, an ASIC (application specific integrated circuit) or FPGA (field programmable gate array), one or more other types of processors implemented in hardware, or some combination thereof. Accordingly, although illustrated in FIG. 2 as a single processor, in some embodiments the processor 200 may comprise a plurality of processors. The plurality of processors may be embodied on a single computing device or may be distributed across a plurality of computing devices collectively configured to function as the healthcare provider apparatus 120. The plurality of processors may be in operative communication with each other and may be collectively configured to perform one or more functionalities of the healthcare provider apparatus 120 as described herein. In some example embodiments, the processor 200 is configured to execute instructions stored in the memory 212 or otherwise accessible to the processor 200. These instructions, when executed by the processor 200, may cause the healthcare provider apparatus 120 to perform one or more of the functionalities of the healthcare provider apparatus 120 as described herein. As such, whether configured by hardware or software methods, or by a combination thereof, the processor 200 may comprise an entity capable of performing operations according to embodiments of the present invention while configured accordingly. Thus, for example, when the processor 200 is embodied as an ASIC, FPGA or the like, the processor 200 may comprise specifically configured hardware for conducting one or more operations described herein. Alternatively, as another example, when the processor 200 is embodied as an executor of instructions, such as may be stored in the memory 212, the instructions may specifically configure the processor 200 to perform one or more algorithms and operations described herein.

The memory 212 may include, for example, volatile and/or non-volatile memory. Although illustrated in FIG. 2 as a single memory, the memory 212 may comprise a plurality of memories. The plurality of memories may be embodied on a single computing device or distributed across a plurality of computing devices. The memory 212 may comprise, for example, a hard disk, random access memory, cache memory, flash memory, an optical disc (e.g., a compact disc read only memory (CD-ROM), digital versatile disc read only memory (DVD-ROM), or the like), circuitry configured to store information, or some combination thereof. In this regard, the memory 212 may comprise any non-transitory computer readable storage medium. The memory 212 may be configured to store information, data, applications, instructions, or the like for enabling the healthcare provider apparatus 120 to carry out various functions in accordance with example embodiments of the present invention. For example, in some example embodiments, the memory 212 is configured to buffer input data for processing by the processor 200. Additionally or alternatively, in some example embodiments, the memory 212 is configured to store program instructions for execution by the processor 200. The memory 212 may store information in the form of static and/or dynamic information. For example, the memory 212 may store symmetric encryption/decryption keys that may be used to encrypt/decrypt electronic health record documents. This stored information may be stored and/or used by the processor 200 during the course of performing its functionalities.

The communication interface 214 may be embodied as any device or means embodied in circuitry, hardware, a computer program product comprising computer readable program instructions stored on a computer readable medium (e.g., the memory 212) and executed by a processing device (e.g., the processor 200), or a combination thereof that is configured to receive and/or transmit data from/to another device, such as, for example, a storage device 110, patient terminal 130, and/or the like. In some example embodiments, the communication interface 214 is at least partially embodied as or otherwise controlled by the processor 200. In this regard, the communication interface 214 may be in communication with the processor 200, such as via a bus. The communication interface 214 may include, for example, an antenna, a transmitter, a receiver, a transceiver and/or supporting hardware or software for enabling communications with another computing device. The communication interface 214 may be configured to receive and/or transmit data using any protocol that may be used for communications between computing devices. As an example, the communication interface 214 may be configured to receive and/or transmit data using any protocol and/or communications technology that may be used for communicating over the network 108. The communication interface 214 may additionally be in communication with the memory 212, and/or user interface 216, such as via a bus.

The user interface 216 may be in communication with the processor 200 to receive an indication of user input (e.g., via user input 220) and/or to provide an audible, visual (e.g., via display 218), tactile, or other output to a user. As such, the user interface 216 may include a user input 220 such as a keyboard user input, a mouse, a joystick, a display 218 which may be a touch screen display, a microphone, a speaker, and/or other input/output mechanisms. The user interface may 216 be implemented to provide a healthcare provider with an interface with an electronic health record and to enable modification of at least portions thereof.

As will be described in further detail below, the healthcare provider apparatus 120 may provide several services in order to facilitate the provision of network-accessible patient health records in accordance with various example embodiments. The healthcare provider apparatus 120 may serve as an access arbiter to facilitate maintaining the security of electronic health record documents stored in the storage device 110. In this regard, in some example embodiments, the healthcare provider apparatus 120 functions as an authority responsible for credentialing and certifying participating entities' identities for authentication exchanges. For example, the healthcare provider apparatus 120 may be configured to authenticate a healthcare provider seeking access to a patient's electronic health record document that may be stored in the storage device 110 to ensure that the healthcare provider has access permissions for viewing at least a portion of the patient's medical data. It will be appreciated that any appropriate authentication protocol considered sufficiently strong to protect security of patient's electronic health record documents may be used for authentication of a healthcare provider. By way of example, any authentication protocol used for authentication in commercial business-to-business interactions may be used.

Further attendant to its security functions, in some example embodiments, the healthcare provider apparatus 120 may assume management of a Public Key Infrastructure (PKI) that may be used to facilitate provisioning of encryption and/or decryption keys (e.g., symmetric keys) to service providers publishing and/or accessing patient health record documents. In some example embodiments, the healthcare provider apparatus 120 may be configured to manage the provisioning of healthcare providers and/or other entities of the system 100 with their public key certificates that may be used for secure information exchange, such as exchange of symmetric keys between the healthcare provider apparatus 120 and storage device 110.

As described above, healthcare information contained in a person's electronic medical record can contain sensitive, private information. As such, access to patient information in the United States is regulated by HIPAA to provide a minimum level of protections that are afforded personal healthcare data. Electronic Health Records (EHRs) contain Electronic Protected Health Information (EPHI) such that any entity used to access this information is required to comply with the most current standard of the HIPAA Security Rule. Each time a patient record is accessed or viewed, the HIPAA Security Rule requires logging the viewing event based on the authorized user accessing the information, the time and date, and potentially the location from which the record was accessed.

Each electronic health record and patient identifier may be encrypted to protect the identity and privacy of the patient. Whenever a patient identifier and/or electronic health record is decrypted, that event must be logged, e.g., in storage device 110, as an access event to the patient identifier and/or electronic health record. In a healthcare provider environment, it is often necessary to search for a patient's record in order to view, modify, or otherwise update that record. When searching for a patient, a user may enter one or more characters from the patient's name, often the last name or surname. However, searching of encrypted information has added complexities. In particular, the one or more characters of the patient's name that are entered may require that the names of all of the patients in the database being searched be decrypted in order to compare the search string characters against the decrypted names. This added complexity increases the time required to conduct a basic search of encrypted patient identifiers and/or electronic health records, particularly in large databases.

Additionally, as noted above, the decryption of all of the names and/or records of the patients in the database requires logging of each decrypted name together with the accessed time and date, and the user who accessed the records. This logging can consume large portions of processing power of a computing resource, such as processor 200, and may consume substantial bandwidth across a network, such as network 108. Considering the frequency with which patient names are searched, such as with locating a patient name and record for scheduling a procedure or appointment, the amount of logging of information quickly escalates. Further, protected, encrypted data belonging to patients that are not the target of the search is accessed unnecessarily.

Disclosed herein is a method of searching for patient identifiers and/or records through the use of truncated encrypted searching. The disclosed methods reduce the bandwidth required by searches and substantially reduces the amount of logging that is required while maintaining compliance with HIPAA privacy rules.

According to an example embodiment, patient identifiers, such as patient names, may be stored in an encrypted format with the patient's electronic health record, for example in storage device 110. Additionally, the database containing the patient names may include a plurality of additional, searchable fields for each patient. A first one of the additional fields may include a first subset of characters of the patient identifier in encrypted format. This may be, for example, the first character of the patient's surname in encrypted format. A second one of the additional fields may include a second subset of characters of the patient identifier in encrypted format. This may be, for example, a first character and a second character of the patient's surname in encrypted format. A third field may include a third subset of characters of the patient identifier in encrypted format. This may be, for example, a first, second, and third character of the patient's surname in encrypted format. Additional fields may be included with additional subsets of characters of the patient identifiers in encrypted format. The number of fields and subsets of characters of a patient identifier may be determined, for example, based on the number of patients in the database such that an increase in the number of fields will reduce the number of patient records accessed during a search, as will be apparent in view of the following disclosure.

According to some embodiments, as outlined above, the first subset of characters of a patient identifier may include only a single character, such as the first character or letter of a patient's surname. The second subset of characters of a patient identifier may include the first and second characters or letters of a patient's surname; however, according to some embodiments, the second subset may include only a single character, which may be the second letter of the patient's surname. Similarly, the third subset of characters may include a sequence of characters from a patient identifier, or may include the third character or letter of a patient's name. Whether single characters are used as the subset of characters or multiple characters are used, embodiments described herein may be implemented with minor differences.

When a user, such as an authorized healthcare provider, conducts a search for a patient electronic health record in a database, such as in storage device 110, using the methods disclosed herein, the user may enter, e.g., via user interface 216, one or more characters from the beginning of the surname of the patient being searched for. In one example embodiment, the first subset of characters is a single character, and that character is the first character of a patient's surname. When one character is entered as the search string, the single character may be encrypted, e.g., by processor 200 or at a processor of storage device 110, and compared against the first field of the database including the first letter of the patient's surname in encrypted format for each patient in the database. This enables the search to filter the total population of patients in the database to only patients including a matching first character of their surname without decrypting any identifiers. The patient identifiers and/or records of those patients where the encrypted first character of the last name matches the encrypted character of the search may be decrypted for the user to review in order to find the specific patient they are seeking. This method reduces the number of patient identifiers and/or records that are decrypted from a total population to only those of the population with a searched first character of their surnames, such that the amount of processing power needed to decrypt the patient identifiers or records is substantially reduced. Further, the amount of logging required is commensurately reduced since the majority of names in the database do not require decryption and therefore are not considered to be "accessed" according to the HIPAA Security Rule.

While the aforementioned embodiment describes a single character search string, embodiments may use more than one character in a search string to further reduce the number of patient identifiers and/or records that require decryption and logging. For example, if a user enters three characters as a search string into a search for a patient, e.g., via user interface 216 of healthcare provider apparatus 120, those three characters may be encrypted and compared against the encrypted first three characters of a patient's surname as found in the aforementioned third field of the database of storage device 110. The encryption may be performed by processor 200 of the healthcare provider apparatus 120, or alternatively, at a processor of storage device 110. This would result in the user being presented only those patients whose first three characters of their last names match the first three characters of the search string.

In an example embodiment in which a single letter is used to identify the first character of a patient's surname, the search is eliminating 25 other options for first characters of the last name of a patient. If two letters are used to identify the first two characters of a patient's surname, 675 alternative combinations of letters are eliminated from potential matches. If three letters are used to identify the first three characters of a patient's surname, over 17,500 alternative combinations of letters are eliminated from potential matches. Therefore, as the number of characters searched is increased, the number of patient identifiers and/or records that are required to be decrypted for review by a user is reduced dramatically. Thus, the processing resources required for decryption and the bandwidth and storage space required for logging of decrypted patient identifiers is drastically reduced.

According to some embodiments, a search string may be longer than the number of characters separately encrypted for searching purposes in the database. For example, a search string may include five characters, while the additional encrypted fields stored in the database of storage device 110 only include up to three characters of a patient's surname. In such an embodiment, the first three characters of the search string may be extracted (i.e., as the extracted subset of characters from the search string) and encrypted to search the field of the database including the encrypted first three characters of the surnames of the patients.

While the aforementioned examples include fields within a database containing one, two, or three, encrypted characters of a patient's surname, embodiments may include any number of characters of the surnames of the patients of the database. Further, the searchable fields may not include multiple encrypted characters, but may include encrypted individual characters of different positions in a patients surname. For example, the first field of the database may include the encrypted first letter of the patient's surname, while the second field includes only the encrypted second letter of the patient's surname. The third field may include only the encrypted third letter of the patient's surname, and so on. In conducting a search according to this embodiment, the search string may be parsed for a first letter, second letter, and third letter, etc. Each of the letters may be separately encrypted and the search conducted in a sequence. The search may initially compare the first encrypted character of the search string with the first field. If the first field matches, then the search may compare the second encrypted character of the search string with the second field of only those for which the first field was a match, and so on. This search may effectively produce the same benefits as those described above with concatenated encrypted letters in fields in the database.

Figure 3:
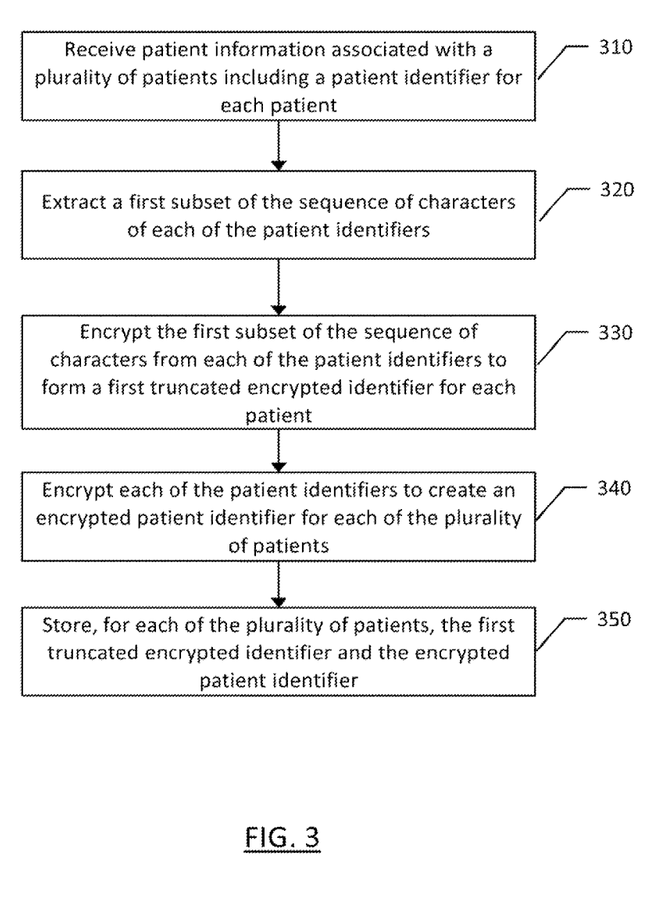
FIG. 3 illustrates a flowchart of a method for creating truncated, encrypted identifiers for a patient record according to an example embodiment.

FIG. 3 illustrates a flowchart of a method for generating a database suitable for conducting truncated encrypted searching. The method of the illustrated embodiment includes receiving patient information associated with a plurality of patients including a patient identifier for each patient at 310. This patient information may be stored, for example, in a database on storage device 110. A first subset of the sequence of characters of each of the patient identifiers is extracted at 320, e.g., by a processor. The first subset of the sequence of characters may be encrypted to form a first truncated encrypted identifier for each patient at 330 by the processor. At 340, each of the patient identifiers may be encrypted by the processor to create an encrypted patient identifier for each of the plurality of patients. For each of the plurality of patients, the corresponding first truncated encrypted identifier and the encrypted patient identifier may be stored in a database at 350.

Figure 4:
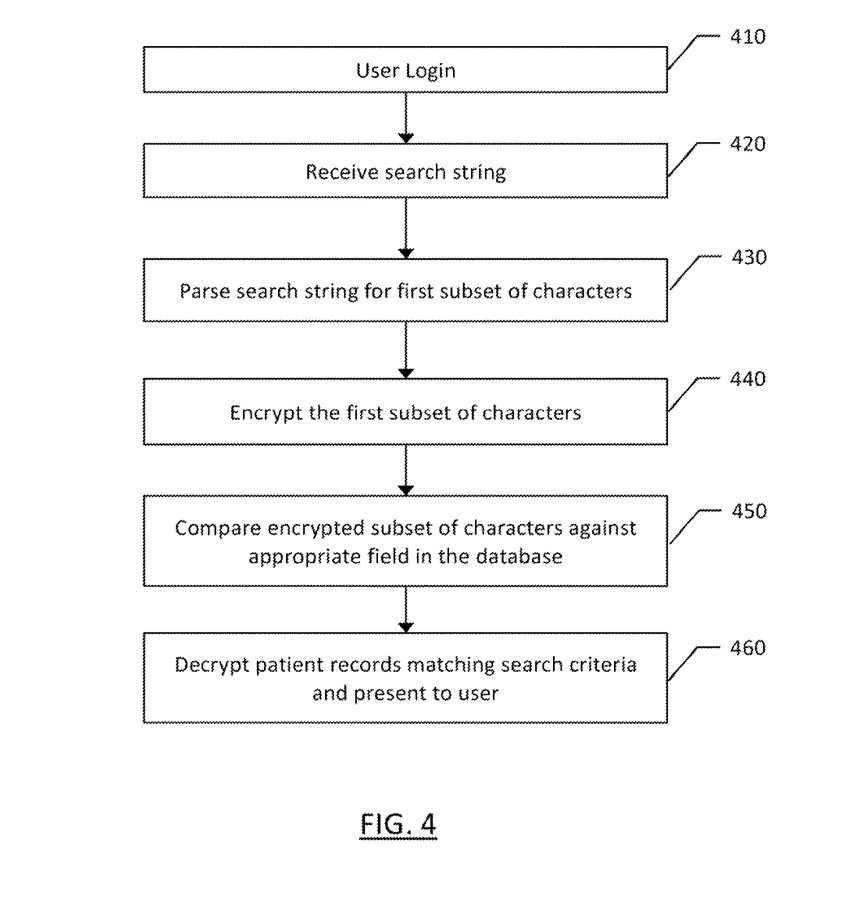
FIG. 4 illustrates a flowchart of a method for searching for a patient record using truncated, encrypted identifiers according to an example embodiment.

The database created at operation 350 may be stored, for example, in storage device 110. This database may be searched by users to find the electronic health record of a particular patient. The storage of the encrypted patient identifier and the truncated encrypted identifier alters the storage device 110 based upon the information stored therein. FIG. 4 illustrates a flow chart of a method for conducting truncated encrypted searching according to an example embodiment. The method may begin with a user login at 410, such as through user interface 216 of FIG. 2, to authenticate, e.g., by processor 200, the authority of the user to access sensitive patient healthcare information. Once successfully logged in, the user may enter a search string (e.g., via user input 220), received at 420. The search string may be a portion of a name of a patient or a patient name in its entirety. The search string may be parsed, by the processor 200, to obtain a first subset of characters of the search string at 430. The parsing may select one or more characters of the search string, and it may be part or all of the search string that is entered. At 440, the first subset of characters may be encrypted by the processor 200 of healthcare provider apparatus 120 or at a processor of storage device 110 to form a truncated encrypted search string. At 450, the truncated encrypted search string of the encrypted subset of characters of the search string may be compared against the appropriate field of the database. The appropriate field of the database may be selected, for example, by the number of characters parsed to create the first subset of characters. If the first subset of characters includes two characters, the appropriate field of the database may contain a subset of two characters from the patient identifier in encrypted format. At 460, the patient records where the truncated encrypted search string matched the truncated encrypted identifier may be returned for review by the user, e.g., on display 218, in order to select the patient record that was sought.

FIGS. 3 and 4 each illustrate a flowchart of a system, method, and computer program product according to example embodiments of the invention. It will be understood that each block of the flowcharts, and combinations of blocks in the flowcharts, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may be stored by one or more memory devices of a server, desktop computer, laptop computer, mobile computer, or other computing device (e.g., healthcare provider apparatus 120, storage device 110, some combination thereof, and/or the like) and executed by a processor (e.g., the processor 200) in the computing device. In some embodiments, the computer program instructions comprising the computer program product(s) which embody the procedures described above may be stored by memory devices of a plurality of computing devices. As will be appreciated, any such computer program product may be loaded onto a computer or other programmable apparatus to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product comprises an article of manufacture which implements the function specified in the flowchart block(s). The computer program instructions of one or more computer program products may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks or steps of the flowcharts support combinations of means for performing the specified functions and combinations of steps for performing the specified functions. It will also be understood that one or more blocks of the flowcharts, and combinations of blocks in the flowcharts, may be implemented by special purpose hardware-based computer systems which perform the specified functions or steps, or combinations of special purpose hardware and computer program product(s).

The above described functions may be carried out in many ways. For example, any suitable means for carrying out each of the functions described above may be employed to carry out embodiments of the invention. In one embodiment, a suitably configured processor may provide all or a portion of the elements of the invention. In another embodiment, all or a portion of the elements of the invention may be configured by and operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

Many modifications and other embodiments of the inventions set forth herein will come to mind to one skilled in the art to which these inventions pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A secure patient information database system, the system comprising at least one processor, wherein the at least one processor is configured to cause the system to at least:

receive patient information associated with a plurality of patients and comprising a patient identifier for each of the plurality of patients, where the patient identifier comprises a sequence of characters;

extract a first subset of the sequence of characters comprising a first number of characters from each of the patient identifiers;

encrypt the first subset of the sequence of characters from each of the patient identifiers to form a first truncated encrypted identifier for each of the plurality of patients;

extract a second subset of the sequence of characters comprising a second number of characters from each of the patient identifiers, wherein the second subset comprises the first subset and at least one additional character;

encrypt the second subset of the sequence of characters from each of the patient identifiers to form a second truncated encrypted identifier for each of the plurality of patients;

encrypt each of the patient identifiers to create an encrypted patient identifier for each of the plurality of patients;

store, for each of the plurality of patients, the first truncated encrypted identifiers, the second truncated encrypted identifiers, and the encrypted patient identifiers;

receive a search request comprising a search string of one or more characters;

encrypt a number of characters of the search string equal to the first number of characters to create an encrypted search string in response to the search string comprising at least the first number of characters, but less than the second number of characters; and encrypt a number of characters of the search string equal to the second number of characters to create an encrypted search string in response to the search string comprising at least the second number of characters.

2. The secure patient information database system of claim 1, wherein the first subset of the sequence of characters comprises at least one but less than all of the characters of the respective patient identifier.

3. The secure patient information database system of claim 2, wherein the processor is further configured to cause the system to:

extract a third subset of the sequence of characters comprising a third number of characters from each of the patient identifiers, wherein the third number of characters is greater than the second number of characters;

encrypt the third subset of the sequence of characters from each of the patient identifiers to form a third truncated encrypted identifier for each of the plurality of patients; and store, for each of the plurality of patients, the third truncated encrypted identifier.

4. The secure patient information database system of claim 1, wherein the processor is further configured to cause the system to:

compare the encrypted search string against the first truncated encrypted identifiers in response to the encrypted search string being encrypted from the first number of characters; and compare the encrypted search string against the second truncated encrypted identifiers in response to the encrypted search string being encrypted from the second number of characters.

5. The secure patient information database system of claim 4, wherein the processor is further configured to cause the system to:

decrypt only the encrypted patient identifiers for each of the plurality of patients for which the first or second truncated encrypted identifier matches the first or second encrypted search string.

6. The secure patient information database system of claim 5, wherein the processor is further configured to cause the system to:

provide for presentation of the patient identifiers for each of the plurality of patients for which the first or second truncated encrypted identifier matches the first or second encrypted search string.

7. A method for providing network-accessible patient health records comprising:

receiving patient information associated with a plurality of patients and comprising a patient identifier for each of the plurality of patients, where the patient identifier comprises a sequence of characters;

extracting a first subset of the sequence of characters comprising a first number of characters from each of the patient identifiers;

encrypting the first subset of the sequence of characters from each of the patient identifiers to form a first truncated encrypted identifier for each of the plurality of patients;

extracting a second subset of the sequence of characters comprising a second number of characters from each of the patient identifiers, wherein the second subset comprises the first subset and at least one additional character;

encrypting the second subset of the sequence of characters from each of the patient identifiers to form a second truncated encrypted identifier for each of the plurality of patients;

encrypting each of the patient identifiers to create an encrypted patient identifier for each of the plurality of patients;

storing, for each of the plurality of patients, the first truncated encrypted identifiers, the second truncated encrypted identifiers, and the encrypted patient identifiers;

receiving a search request comprising a search string of one or more characters;

encrypting a number of characters of the search string equal to the first number of characters to create an encrypted search string in response to the search string comprising at least the first number of characters, but less than the second number of characters; and encrypting a number of characters of the search string equal to the second number of characters to create an encrypted search string in response to the search string comprising at least the second number of characters.

8. The method for providing network-accessible patient health records of claim 7, wherein the first subset of the sequence of characters comprises at least one but less than all of the characters of the respective patient identifier.

9. The method for providing network-accessible patient health records of claim 8, further comprising:

extracting a third subset of the sequence of characters comprising a third number of characters from each of the patient identifiers, wherein the third number of characters is greater than the second number of characters;

encrypting the third subset of the sequence of characters from each of the patient identifiers to form a third truncated encrypted identifier for each of the plurality of patients; and storing, for each of the plurality of patients, the third truncated encrypted identifiers.

10. The method for providing network-accessible patient health records of claim 7, further comprising:

comparing the encrypted search string against the first truncated encrypted identifiers in response to the encrypted search string being encrypted from the first number of characters; and comparing the encrypted search string against the second truncated encrypted identifiers in response to the encrypted search string being encrypted from the second number of characters.

11. The method for providing network-accessible patient health records of claim 10, further comprising:
   decrypting only the encrypted patient identifiers for each of the plurality of patients for which the first or second truncated encrypted identifier matches the first or second encrypted search string.

12. The method for providing network-accessible patient health records of claim 11, further comprising:
   providing for presentation of the patient identifiers for each of the plurality of patients for which the first or second truncated encrypted identifier matches the first or second encrypted search string.

13. A computer program product for providing network-accessible patient health records, the computer program product comprising at least one non-transitory computer-readable storage medium having computer-readable program code instructions stored therein, the computer-readable program code instructions comprising:
   program code instructions for receiving patient information associated with a plurality of patients and comprising a patient identifier for each of the plurality of patients, where the patient identifier comprises a sequence of characters;
   program code instructions for extracting a first subset of the sequence of characters comprising a first number of characters from each of the patient identifiers;
   program code instructions for encrypting the first subset of the sequence of characters from each of the patient identifiers to form a first truncated encrypted identifier for each of the plurality of patients;
   program code instructions for extracting a second subset of the sequence of characters comprising a second number of characters from each of the patient identifiers, wherein the second subset comprises the first subset and at least one additional character;
   program code instructions for encrypting the second subset of the sequence of characters from each of the patient identifiers to form a second truncated encrypted identifier for each of the plurality of patients;
   program code instructions for encrypting each of the patient identifiers to create an encrypted patient identifier for each of the plurality of patients;
   program code instructions for storing, for each of the plurality of patients, the first truncated encrypted identifiers, the second truncated encrypted identifiers, and the encrypted patient identifiers;
   program code instructions for receiving a search request comprising a search string of one or more characters;
   program code instructions for encrypting a number of characters of the search string equal to the first number of characters to create an encrypted search string in response to the search string comprising at least the first number of characters, but less than the second number of characters; and
   program code instructions for encrypting a number of characters of the search string equal to the second number of characters to create an encrypted search string in response to the search string comprising at least the second number of characters.

14. The computer program product of claim 13, wherein the first subset of the sequence of characters comprises at least one but less than all of the characters of the respective patient identifier.

15. The computer program product of claim 14, further comprising:
   program code instructions for extracting a third subset of the sequence of characters comprising a third number of characters from each of the patient identifiers, wherein the third number of characters is greater than the second number of characters;
   program code instructions for encrypting the third subset of the sequence of characters from each of the patient identifiers to form a third truncated encrypted identifier for each of the plurality of patients; and
   program code instructions for storing, for each of the plurality of patients, the third truncated encrypted identifiers.

16. The computer program product of claim 13, further comprising:
   program code instructions for comparing the encrypted search string against the first truncated encrypted identifiers in response to the encrypted search string being encrypted from the first number of characters; and
   program code instructions for comparing the encrypted search string against the second truncated encrypted identifiers in response to the encrypted search string being encrypted from the second number of characters.

17. The computer program product of claim 16, further comprising:
   program code instructions for decrypting only the encrypted patient identifiers for each of the plurality of patients for which the first or second truncated encrypted identifier matches the first or second encrypted search string.

* * * * *